(12) United States Patent
Almogy et al.

(10) Patent No.: US 6,861,660 B2
(45) Date of Patent: Mar. 1, 2005

(54) PROCESS AND ASSEMBLY FOR NON-DESTRUCTIVE SURFACE INSPECTION

(75) Inventors: Gilad Almogy, Givatayim (IL); Ron Naftali, Shoham (IL); Avishay Guetta, Rehovot (IL); Doron Shoham, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 42 days.

(21) Appl. No.: 10/208,113

(22) Filed: Jul. 29, 2002

(65) Prior Publication Data

US 2004/0016896 A1 Jan. 29, 2004

(51) Int. Cl.⁷ .............................................. G01N 21/88
(52) U.S. Cl. ................................ 250/559.45; 356/237.2
(58) Field of Search ..................... 250/559.45, 559.41; 356/237.4, 237.5, 237.3, 237.2; 382/144, 145

(56) References Cited

U.S. PATENT DOCUMENTS

| | | | |
|---|---|---|---|
| 4,598,997 A | 7/1986 | Steigmeier et al. | |
| 4,957,367 A | 9/1990 | Dulman | |
| 5,572,598 A | 11/1996 | Wihl et al. | |
| 5,659,390 A | 8/1997 | Danko | |
| 6,271,916 B1 | 8/2001 | Marxer et al. | |
| 6,538,730 B2 * | 3/2003 | Vaez-Iravani et al. | ... 356/237.2 |

FOREIGN PATENT DOCUMENTS

| | | |
|---|---|---|
| DE | 41 34 747 A1 | 4/1993 |
| WO | WO 99/14575 | 3/1999 |
| WO | WO 99/56113 | 11/1999 |
| WO | WO 01/98755 A2 | 12/2001 |

OTHER PUBLICATIONS

PCT International Search Report for PCT/US 03/ 22786, mailed Oct. 12, 2003, 8 pages.

* cited by examiner

Primary Examiner—Thanh X. Luu
Assistant Examiner—Seung C. Sohn
(74) Attorney, Agent, or Firm—Blakely, Sokoloff, Taylor & Zafman

(57) ABSTRACT

An optical system for detecting defects on a wafer that includes a device for producing a beam and directing the beam onto the wafer surface, producing an illuminated spot on the wafer's surface. The system further includes a detector detecting light, and a mirrored assembly having together with the detector an axis of symmetry about a line perpendicular to the wafer surface. The assembly is configured to receive scattered light from the surface, where the scattered light including a first scattered light part being scattered from the pattern. The assembly is further configured to reflect and focus rotationally symmetrically about the axis of symmetry the scattered light to the detector. The system further includes a device operating with the detector for facilitating detection of a scattered light other than the specified scattered light due to pattern.

2 Claims, 13 Drawing Sheets

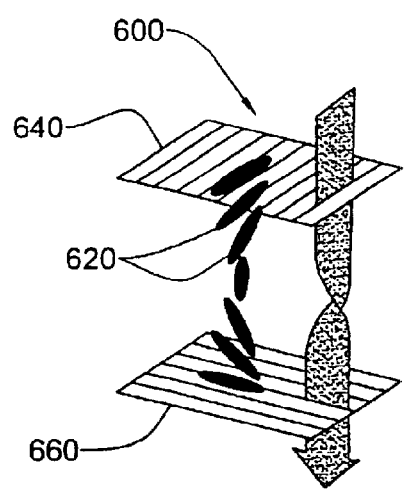
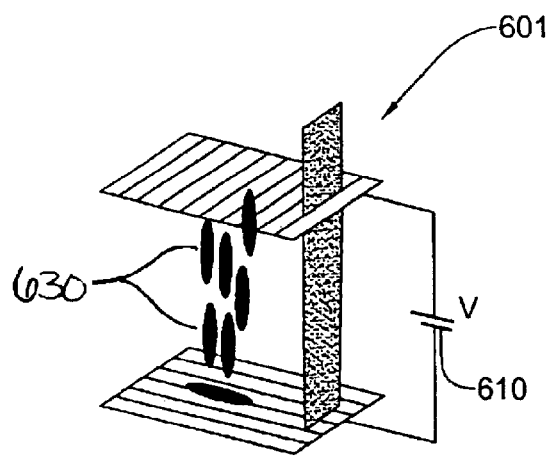
FIG. 5A          FIG. 5B
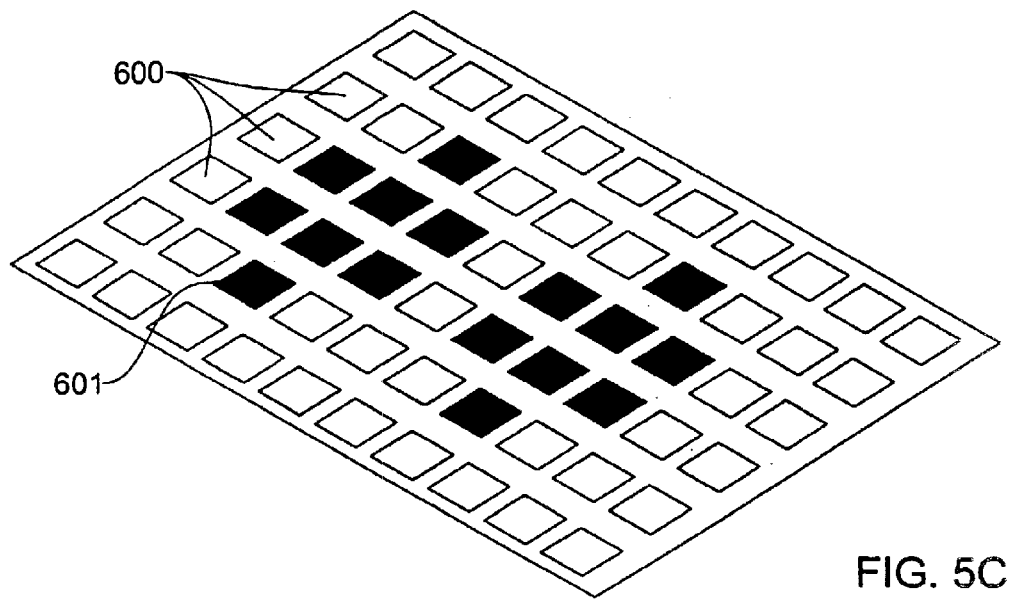
FIG. 5C

PROCESS AND ASSEMBLY FOR NON-DESTRUCTIVE SURFACE INSPECTION

FIELD OF THE INVENTION

The invention relates to the field of optical inspection. More specifically, the invention relates to the inspection of surfaces and in particular to detecting defects in semiconductor patterned wafers.

BACKGROUND OF THE INVENTION

The detection of defects on the surface of semiconductor wafers due to imperfect production or the post-production adhesion process has received considerable attention in the art. Generally, wafers fall into two main categories, "unstructured" (or "unpatterned") and "patterned". A patterned wafer has circuit patterns ("dies") imprinted on it, while an unstructured (unpatterned) wafer is still bare, i.e. with no circuits imprinted on it as yet.

Generally speaking, numerous systems and methods have been developed to cope with the problem of defect detection and in particular, for the non-destructive inspection of silicon wafers. A prior art system known as the "Excite System" of Applied Materials includes a light beam source and an optical system that projects the beam onto the test object, as well as means for detecting the reflected and/or scattered light. There is an additional assembly for moving the test object in a coordinated translational and rotary movement, so that the light spot projected thereon scans the whole surface along a spiral path. The detected scattered light is analyzed in order to determine the sought defects.

The development of processes enabling the manufacture of wafer surfaces with ever-finer structures, urged the development of inspection systems for the detection of ever more minute defects such as particle contamination, polishing scratches, variations in the thickness of coatings, roughness, crystal defects on and below the surface, etc. Insofar as unstructured wafers are concerned, they are subjected to a thorough searching examination for detecting said defects.

In the chip manufacturing process, it is common to monitor each stage in order to recognize problems as early as possible and thus avoid undue waste. When unstructured wafers are compared between two process stages, the types and amount of defects at some stage can be determined. The inspected surface may be rough and metallized, and may therefore produce a great deal of scattered light, or, it may be a film-coated surface with a small amount of defects and produce scattered light. Thus, the inspecting instrument should preferably have a wide dynamic range of detection to permit defect and particle detection of a wide variety of surfaces.

Laser scanners are particularly suitable for that purpose. Note that presently available laser scanners differ in the type of scanning they use, their optical configuration, and the manner in which the results are processed. For applications that require a high throughput and nearly 100% inspection of the whole wafer surface, two processes are mainly used. In the first, disclosed e.g. in U.S. Pat. No. 4,314,763 to Steigmeier & Knop, the illuminating beam and the collecting optics are stationary, and the test object is scanned spirally by means of a coordinated translational and rotary movement of the object itself. In the second process disclosed, e.g. in U.S. Pat. No. 4,378,159 to Galbraith, a rotating or vibrating mirror moves the illuminating beam in one direction linearly back and forth across the wafer, while the wafer is simultaneously translated perpendicular thereto. In general, the first method is simpler and with homogenous accuracy, while the second is faster.

Bearing all that in mind, attention is drawn to U.S. Pat. No. 6,271,916 to Marxer et al. Briefly speaking, the Marxer patent discloses an assembly for non-destructive surface inspections. The system according to the '916 patent will now be briefly described with reference to FIGS. 1A–B. Thus, the apparatus according to the Marxer patent includes a light beam that is directed by a beam deflector 113 and 131 towards the wafer's surface 135, preferably normal thereto. The wafer is moved by a rotation motor 145 and a translation motor 149 according to the technique disclosed in the '159 patent. A circumferential ellipsoidal mirrored surface 127 is placed around the wafer, with its axis coinciding with the surface normal, to collect scattered light from defects at the wafer surface at collection angles away from the surface normal. In some applications, a lens arrangement with its axis coinciding with the surface normal is also used to collect the light scattered by the surface and by any defects on it. The light scattered by the mirror and lenses may be directed to the same or different detectors. Preferably, light scattered by the surface within a first range of collection angles from the axis is detected by a first detector 121, and light scattered by the surface within a second range of collection angles from the axis is detected by a second detector 125 (shown in FIG. 1B only). The two ranges of collection angles are different, with one detector optimized to detect scattering from large defects (mainly large particles) and the other detector optimized to detect light from small defects (particles). The content of the Marxer patent is incorporated herein by reference.

The detectors according to the Marxer patent, detect practically only light scattered from defects, whereas reflected light (reflected from a well-polished surface) is out-guided in order not to interfere with the scattered light received by the detectors. This method of measuring diffused light from defects only is called "dark field".

The apparatus according to the Marxer patent offers a solution applicable, if at all, to the detection of defects on unstructured wafers. However, the specified apparatus of the Marxer patent is not applicable to the detection of defects on patterned wafers, because in the case of patterned wafers, the detectors do not only receive light scattered from defects, but also light scattered from the patterns. Considering that the intensity of the latter is much higher than that of the former, it would be very difficult and in fact practically infeasible to determine whether the received light originates from a defect or from a fault-free pattern.

Die to die defect analysis is based upon a comparison (usually a on a pixel to pixel bases or even a sub-pixel to sub-pixel bases) of pixels originating from light scattered from the same spot on two distinct dies. Die to die comparison require hat substantially the same illumination and collection conditions apply during the generation of the pixels. The Marxer patent does not enable die to die defect analysis as the wafer is rotated during the illumination of the wafer, and both the illumination and collection paths constantly change as result from the wafers rotation. The problem is especially acute when the wafers are patterned and when using dark field detectors to detect defects, as the dark field images are very dependent upon the direction of light scattered from the rotating pattern. Accordingly, there is a need in the art to provide an apparatus that performs defect detection of patterned wafers.

There is another need in the art to provide an apparatus that performs defect detection of both patterned and unpatterned wafers.

There is yet a further need to allow a compact optical inspection apparatus that enables die to die defect analysis.

SUMMARY OF THE INVENTION

The invention provides for an optical system for detecting defects on a wafer that includes at least one pattern; the system comprising:

a source of light to produce a beam;

optics directing the beam along a path onto the wafer, producing an illuminated spot thereon;

at least one detector for detecting light;

an ellipsoidal mirrored surface, said mirrored surface and the at least one detector having an axis of symmetry about a line perpendicular to the wafer surface, said mirrored surface defining an input aperture positioned proximate to the wafer surface to receive scattered light therethrough from the surface; said mirrored surface further defining an exit aperture and being substantially rotationally symmetric about said axis of symmetry, so that the mirrored surface reflects and focuses rotationally symmetrically about said axis of symmetry light that passes through the input aperture to the at least one detector;

said exit aperture being located opposite to the input aperture; and at least one filter located between said exit aperture and said at least one detector and being configured to pass to said at least one detector scattered light rays substantially other than scattered light part being scattered from at least one of said patterns.

The invention enables die to die defect analysis by implementing at least one of the following measures: (i) illuminating the inspected object with a beam that is perpendicular to the surface of the inspected object, whereas the beam cross section is symmetrical and an array of detectors are positioned such as to collect scattered light beams; (ii) using a dove prism; rotating the optical detectors array such as to compensate for the rotation of the wafer.

The invention further provides for an optical system for detecting defects on a wafer that includes at least one pattern; the system comprising:

a source of light to produce a beam;

optics directing the beam along a path onto the wafer surface, producing an illuminated spot thereon;

an array of detectors detecting light;

an ellipsoidal mirrored surface, said mirrored surface and the array of detectors having an axis of symmetry about a line perpendicular to the wafer, said mirrored surface defining an input aperture positioned proximate to the test surface to receive scattered light therethrough from the surface; said mirrored surface further defining an exit aperture and being substantially rotationally symmetric about said axis of symmetry, so that the mirrored surface reflects and focuses rotationally symmetrically about said axis of symmetry light that passes through the input aperture to the array of detectors;

said exit aperture being located between said array of detectors and said input aperture;

said array of detectors are adapted to detect scattered light substantially other than scattered light part being scattered from at least one of said patterns.

Still further, the invention provides for an optical system for detecting defects on a wafer that includes at least one pattern; the system comprising:

a source of light to produce a beam;

optics directing the beam along a path onto the wafer, producing an illuminated spot thereon;

at least one detector for detecting light;

an ellipsoidal mirrored surface, said mirrored surface and the at least one detector having an axis of symmetry about a line perpendicular to the wafer surface, said mirrored surface defining an input aperture positioned proximate to the wafer surface to receive scattered light therethrough from the surface; said mirrored surface further defining an exit aperture and being substantially rotationally symmetric about said axis of symmetry, so that the mirrored surface reflects and focuses rotationally symmetrically about said axis of symmetry light that passes through said input aperture to the at least one detector;

said exit aperture being located opposite to the input aperture;

a Dove prism, having with the at least one detector an axis of symmetry about a line perpendicular to the wafer's surface and parallel to said Dove prism's base, said Dove prism being rotated about said axis of symmetry, so as to rotate light passing through said Dove prism at twice the angular velocity of said Dove prism in the opposite direction about said axis of symmetry; and at least one filter located between said Dove prism and said at least one detector and being configured to pass to said at least one detector scattered light rays substantially other than scattered light part being scattered from at least one of said patterns.

Yet further, an optical system for detecting defects on a wafer that includes at least one pattern; the system comprising:

a source of light to produce a beam;

optics directing the beam along a path onto the wafer, producing an illuminated spot thereon;

an array of detectors for detecting light;

an ellipsoidal mirrored surface, said mirrored surface and the array of detectors having an axis of symmetry about a line perpendicular to the wafer surface, said mirrored surface defining an input aperture positioned proximate to the wafer surface to receive scattered light therethrough from the surface; said mirrored surface further defining an exit aperture and being substantially rotationally symmetric about said axis of symmetry, so that said mirrored surface reflects and focuses rotationally symmetrically about said axis of symmetry light that passes through said input aperture to the array of detectors;

said exit aperture being located opposite to said input aperture;

a Dove prism, said Dove prism and the array of detectors having an axis of symmetry about a line perpendicular to the wafer surface and parallel to said Dove prism's base, said Dove prism being rotated about said axis of symmetry, so as to rotate light passing through said Dove prism at twice the angular velocity of said Dove prism in the opposite direction about said axis of symmetry; said Dove prism further being configured to pass to said array of detectors scattered light rays substantially other than scattered light part being scattered from at least one of said patterns.

The invention provides for an optical system for detecting defects on a wafer that includes at least one pattern; the system comprising:

a source of light to produce a beam;

means for directing the beam along a path onto the wafer, producing an illuminated spot thereon;

at least one means for detecting light;
an ellipsoidal mirrored surface, said mirrored surface and the at least one detecting means having an axis of symmetry about a line perpendicular to the wafer surface, said mirrored surface defining an input aperture positioned proximate to the wafer surface to receive scattered light therethrough from the surface; said mirrored surface further defining an exit aperture and being substantially rotationally symmetric about said axis of symmetry, so that the mirrored surface reflects and focuses rotationally symmetrically about said axis of symmetry light that passes through the input aperture to the at least one detecting means;

said exit aperture being located opposite to the input aperture; and at least one filter located between said exit aperture and said at least one detecting means and being configured to pass to said at least one detecting means scattered light rays substantially other than scattered light part being scattered from at least one of said patterns.

The invention further provides for an optical system for detecting defects on a wafer that includes at least one pattern; the system comprising:
a source of light to produce a beam;
means for directing the beam along a path onto the wafer surface, producing an illuminated spot thereon;

an array of detecting means for detecting light;

an ellipsoidal mirrored surface, said mirrored surface and the array of detecting means having an axis of symmetry about a line perpendicular to the wafer, said mirrored surface defining an input aperture positioned proximate to the test surface to receive scattered light therethrough from the surface; said mirrored surface further defining an exit aperture and being substantially rotationally symmetric about said axis of symmetry, so that the mirrored surface reflects and focuses rotationally symmetrically about said axis of symmetry light that passes through the input aperture to the array of detecting means;

said exit aperture being located between said array of detecting means and said input aperture;

said array of detecting means are adapted to detect scattered light substantially other than scattered light part being scattered from at least one of said patterns.

Still further, the invention provides for an optical system for detecting defects on a wafer, comprising:

a device for producing a beam and directing the beam onto the wafer surface, producing an illuminated spot thereon;

at least one detector detecting light;

a mirrored assembly having together with the at least one detector an axis of symmetry about a line perpendicular to the wafer surface, said assembly is configured to receive scattered light from the surface; said assembly further configured to reflect and focus rotationally symmetrically about said axis of symmetry the scattered light to the at least one detector; and a device associated with said at least one detector for facilitating detection of a scattered light substantially other than scattered light part being scattered from at least one of said patterns.

Yet further, the invention provides for an optical system for detecting defects on a wafer, comprising:

a device for producing a beam and directing the beam onto the wafer surface, producing an illuminated spot thereon;

at least one detector detecting light;

a mirrored assembly configured to receive scattered light from the surface; said assembly further configured to reflect the scattered light to the at least one detector; and a device associated with said at least one detector for facilitating detection of a scattered light substantially other than scattered light part being scattered from at least one of said patterns.

The invention provides for an optical method for detecting defects on a wafer that includes at least one pattern; the method comprising:

providing a beam of light;

directing the beam along a path onto the wafer, producing an illuminated spot thereon;

positioning an ellipsoidal mirrored surface and at least one detector so that they have an axis of symmetry about a line perpendicular to the wafer surface, said mirrored surface defining an input aperture positioned proximate to the wafer surface to receive scattered light therethrough from the surface; said mirrored surface further defining an exit aperture and being substantially rotationally symmetric about said axis of symmetry, so that the mirrored surface reflects and focuses rotationally symmetrically about said axis of symmetry light that passes through the input aperture to the at least one detector; said exit aperture being located opposite to the input aperture; and locating at least one filter between said exit aperture and said at least one detector, configuring the at least one filter to pass to said at least one detector scattered light rays substantially other than scattered light part being scattered from at least one of said patterns.

Still further, the invention provides for An optical method for detecting defects on a wafer that includes at least one pattern; the method comprising:

providing a beam of light;

directing the beam along a path onto the wafer surface, producing an illuminated spot thereon;

positioning an ellipsoidal mirrored surface and an array of detectors so that they have an axis of symmetry about a line perpendicular to the wafer, said mirrored surface defining an input aperture positioned proximate to the test surface to receive scattered light therethrough from the surface; said mirrored surface further defining an exit aperture and being substantially rotationally symmetric about said axis of symmetry, so that the mirrored surface reflects and focuses rotationally symmetrically about said axis of symmetry light that passes through the input aperture to the array of detectors; said exit aperture being located between said array of detectors and said input aperture;

adapting said array of detectors to detect scattered light substantially other than scattered light part being scattered from at least one of said patterns.

Yet further, the invention provides for an optical method for detecting defects on a wafer that includes at least one pattern; the method comprising:

providing a beam of light;

directing the beam along a path onto the wafer, producing an illuminated spot thereon;

positioning an ellipsoidal mirrored surface and at least one detector so that they have an axis of symmetry about a line perpendicular to the wafer surface, said mirrored surface defining an input aperture positioned proximate to the wafer surface to receive scattered light therethrough from the surface; said mirrored surface further defining an exit aperture and being substantially rotationally symmetric about said axis of symmetry, so that the mirrored surface reflects and focuses rotationally symmetrically about said axis of symmetry light that passes through said input aperture to the at least one detector; said exit aperture being located opposite to the input aperture;

positioning a Dove prism, so as to have with the at least one detector an axis of symmetry about a line perpendicular to the wafer's surface and parallel to said Dove prism's base; said Dove prism is rotated about said axis of symmetry, so as to rotate light passing through said Dove prism at twice the angular velocity of said Dove prism in the opposite direction about said axis of symmetry; and locating at least one filter between said Dove prism and said at least one detector and configuring the filter to pass to said at least one detector scattered light rays substantially other than scattered light part being scattered from at least one of said patterns.

The invention provides for an optical method for detecting defects on a wafer that includes at least one pattern; the method comprising:

providing a beam of light;

directing the beam along a path onto the wafer, producing an illuminated spot thereon;

positioning an ellipsoidal mirrored surface and an array of detectors so that they have an axis of symmetry about a line perpendicular to the wafer surface, said mirrored surface defining an input aperture positioned proximate to the wafer surface to receive scattered light therethrough from the surface; said mirrored surface further defining an exit aperture and being substantially rotationally symmetric about said axis of symmetry, so that said mirrored surface reflects and focuses rotationally symmetrically about said axis of symmetry light that passes through said input aperture to the array of detectors; said exit aperture being located opposite to said input aperture;

positioning a Dove prism so as to have with the array of detectors an axis of symmetry about a line perpendicular to the wafer surface and parallel to said Dove prism's base; said Dove prism is rotated about said axis of symmetry, so as to rotate light passing through said Dove prism at twice the angular velocity of said Dove prism in the opposite direction about said axis of symmetry; said Dove prism is further being configured to pass to said array of detectors scattered light rays substantially other than scattered light part being scattered from at least one of said patterns.

The invention further provides for an optical method for detecting defects on a wafer, comprising:

providing a device for producing a beam and directing the beam onto the wafer surface so as to produce illuminated spot thereon;

positioning a mirrored assembly and at least one detector so that they have an axis of symmetry about a line perpendicular to the wafer surface; configuring said assembly to receive scattered light from the surface and further configuring said assembly to reflect and focus rotationally symmetrically about said axis of symmetry the scattered light to the at least one detector; and positioning a device associated with said at least one detector for facilitating detection of a scattered light substantially other than scattered light part being scattered from at least one of said patterns.

Yet further, the invention provides for an optical method for detecting defects on a wafer, comprising:

providing a device for producing a beam and directing the beam onto the wafer surface so as to produce an illuminated spot thereon;

positioning a mirrored assembly configured to receive scattered light from the surface and further configuring said assembly to reflect the scattered light to the at least one detector; and positioning a device associated with said at least one detector for facilitating detection of a scattered light substantially other than scattered light part being scattered from at least one of said patterns.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 5A–B illustrate two stages (pass/fail) of a liquid crystal based filter in accordance with an embodiment of the invention;

FIG. 5C shows a filter that is composed of 2D matrix liquid crystal cells, in accordance with an embodiment of the invention;

DETAILED DESCRIPTION OF THE INVENTION

It should be noted that in the context of the invention, the term "defect" should be construed in a broad manner including but not limited to particle contamination, polishing scratches, variations in the thickness of coatings, roughness, crystal defects on and below the surface etc.

A beam of light that impinges on the surface of a patterned wafer produces a reflected beam and multiple scattered rays due to pattern and due to (possible) defects. The distribution of scattered rays due to pattern is distributed substantially different than the distribution of scattered ray due to defects. Thus, knowing in advance the distribution of scattered rays due to pattern, enables one to locate a set of detectors at places where the distribution of scattered rays due to pattern is zero, or at least minimal, or alternatively block the light rays at places where the distribution of rays due to pattern is significant, and by this to detect mainly scattered rays due to defects. This method can be used to verify the presence of defects on a patterned wafer, as will be explained in detail below.

Figure 1A:
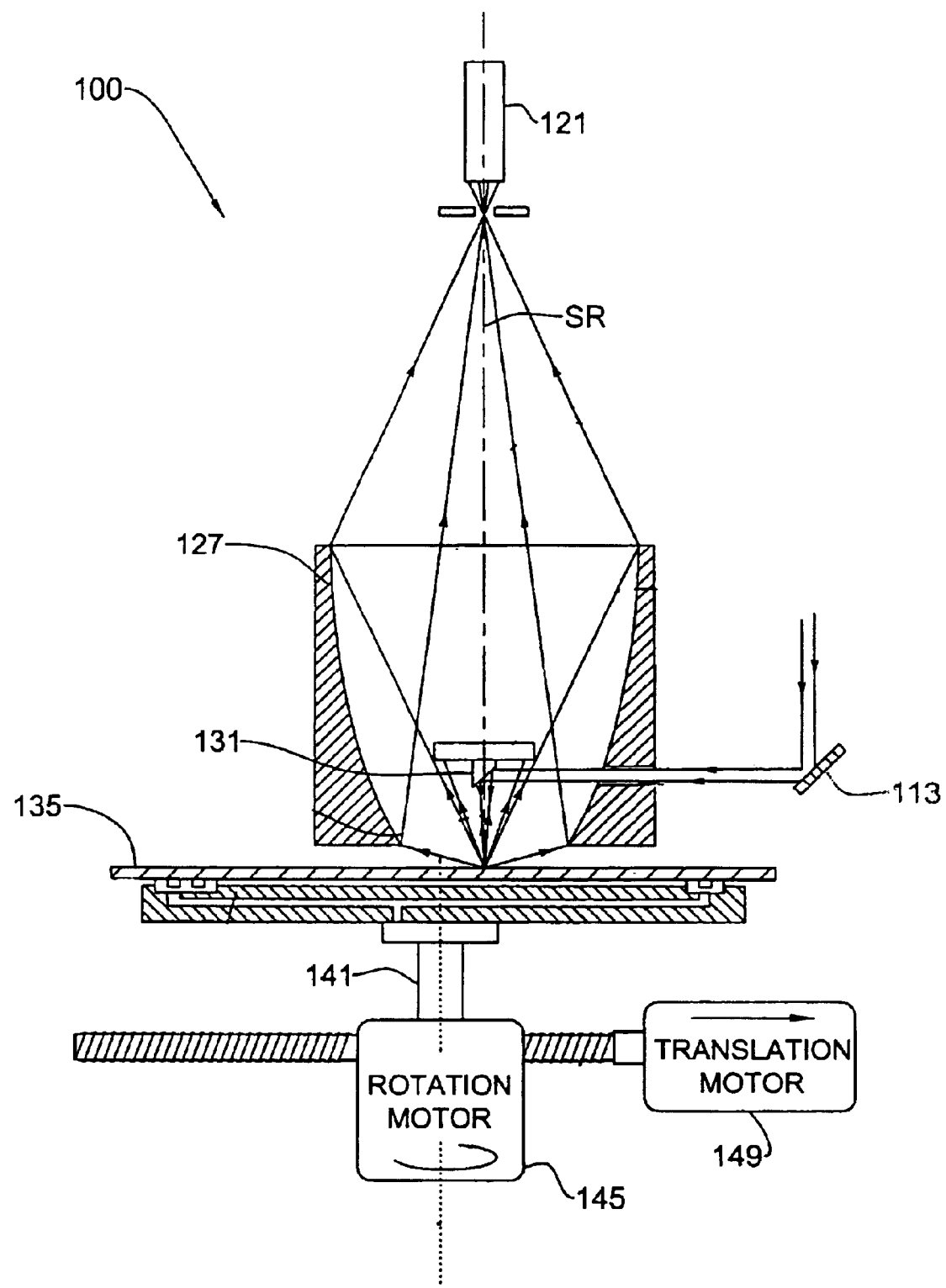
FIGS. 1A–B illustrate schematically two embodiments of an apparatus according to the Marxer patent.
Figure 1B:
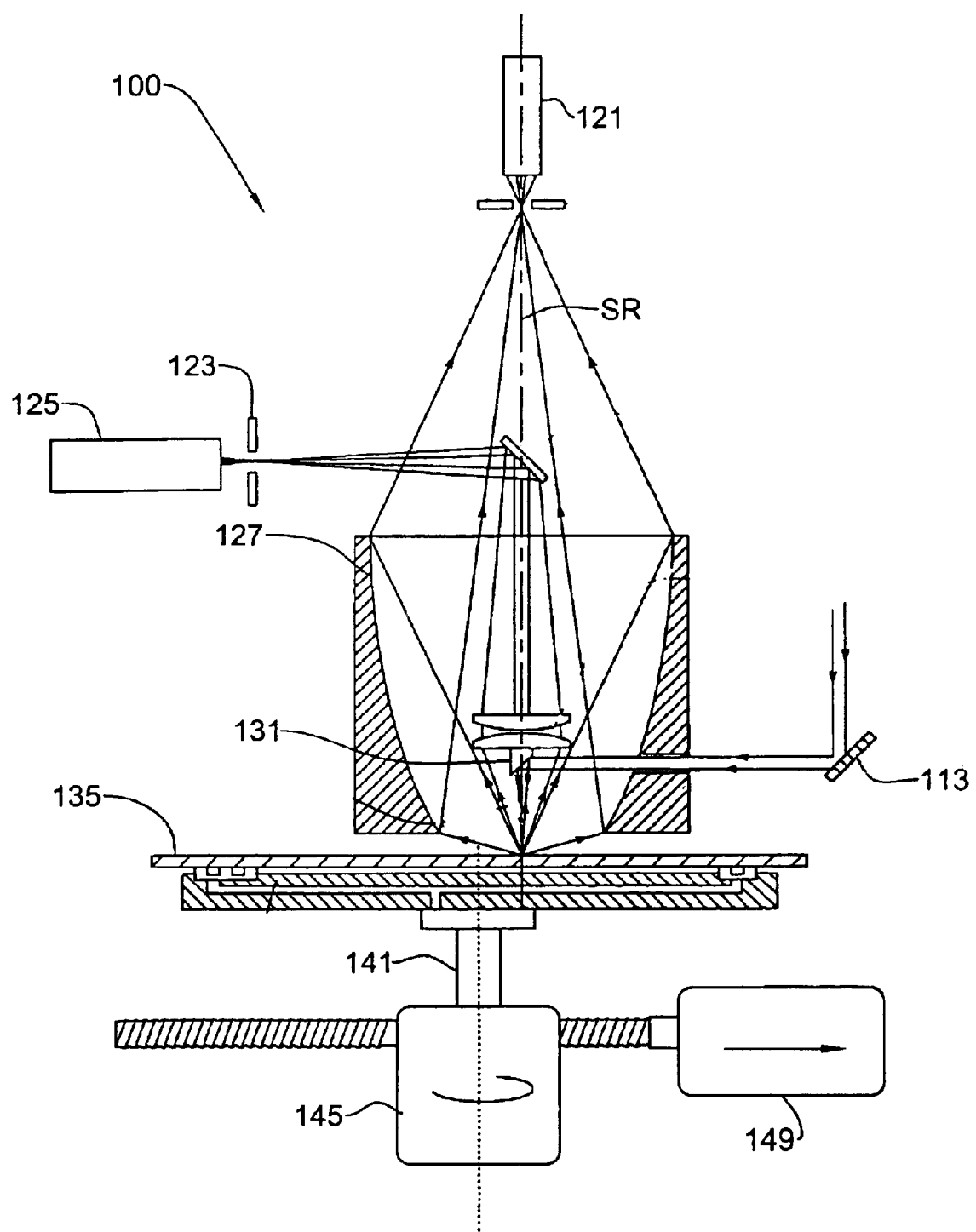
Figure 2A:
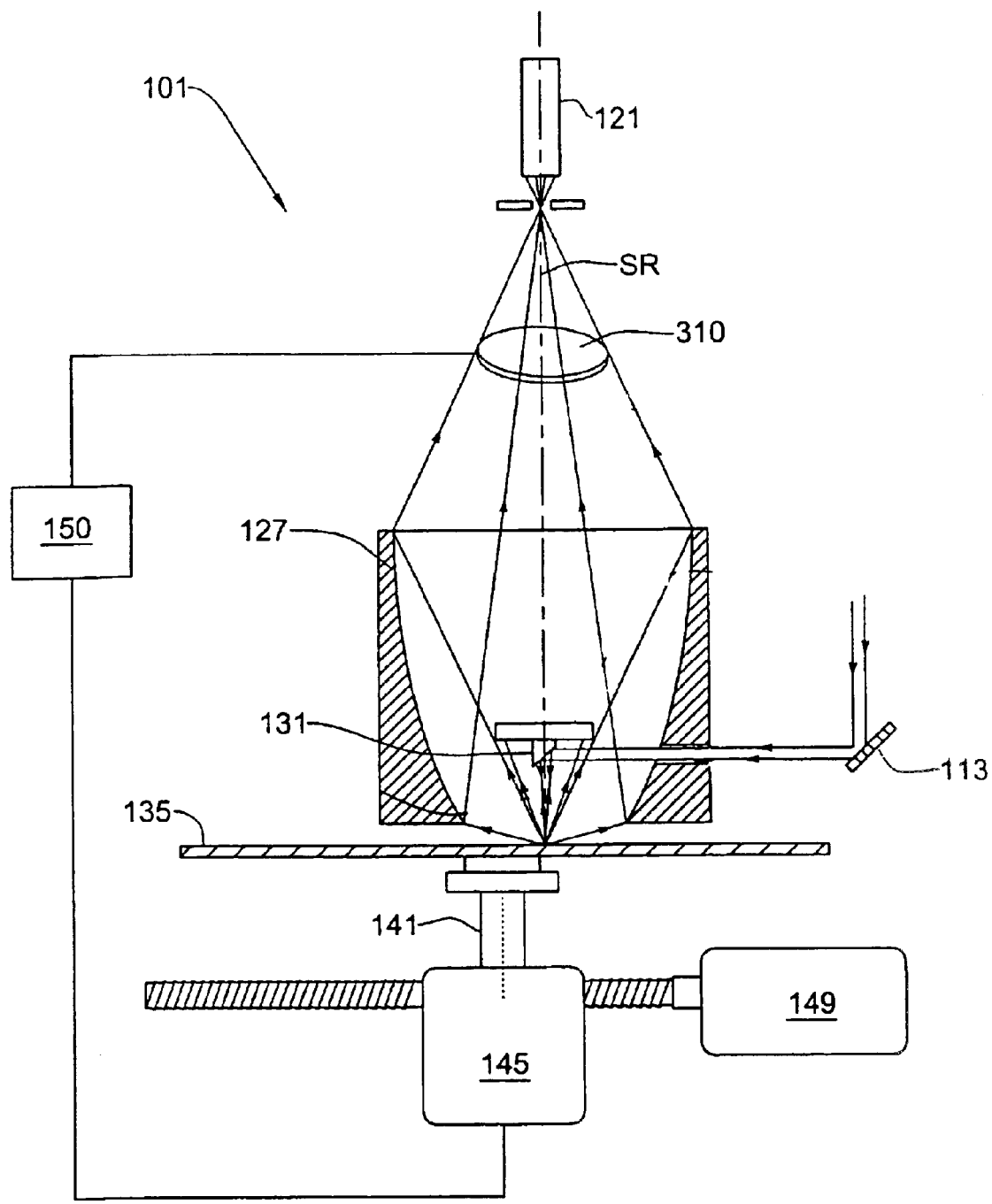
FIG. 2A shows a perspective view of an apparatus according to one embodiment of the present invention.

FIG. 2A shows apparatus 101 according to an embodiment of the present invention. The apparatus differs from that described in U.S. Pat. No. 6,271,916 B1, in that it is operable to detect defects of patterned wafers. Apparatus 101 includes filter 310 that is disposed between an ellipsoidal mirror 127 and a detector 121. The added filter is designed to block the path of scattered light due to the pattern, but simultaneously let the scattered light due to a defect pass through, as will be explained in greater detail below.

Figure 2B:
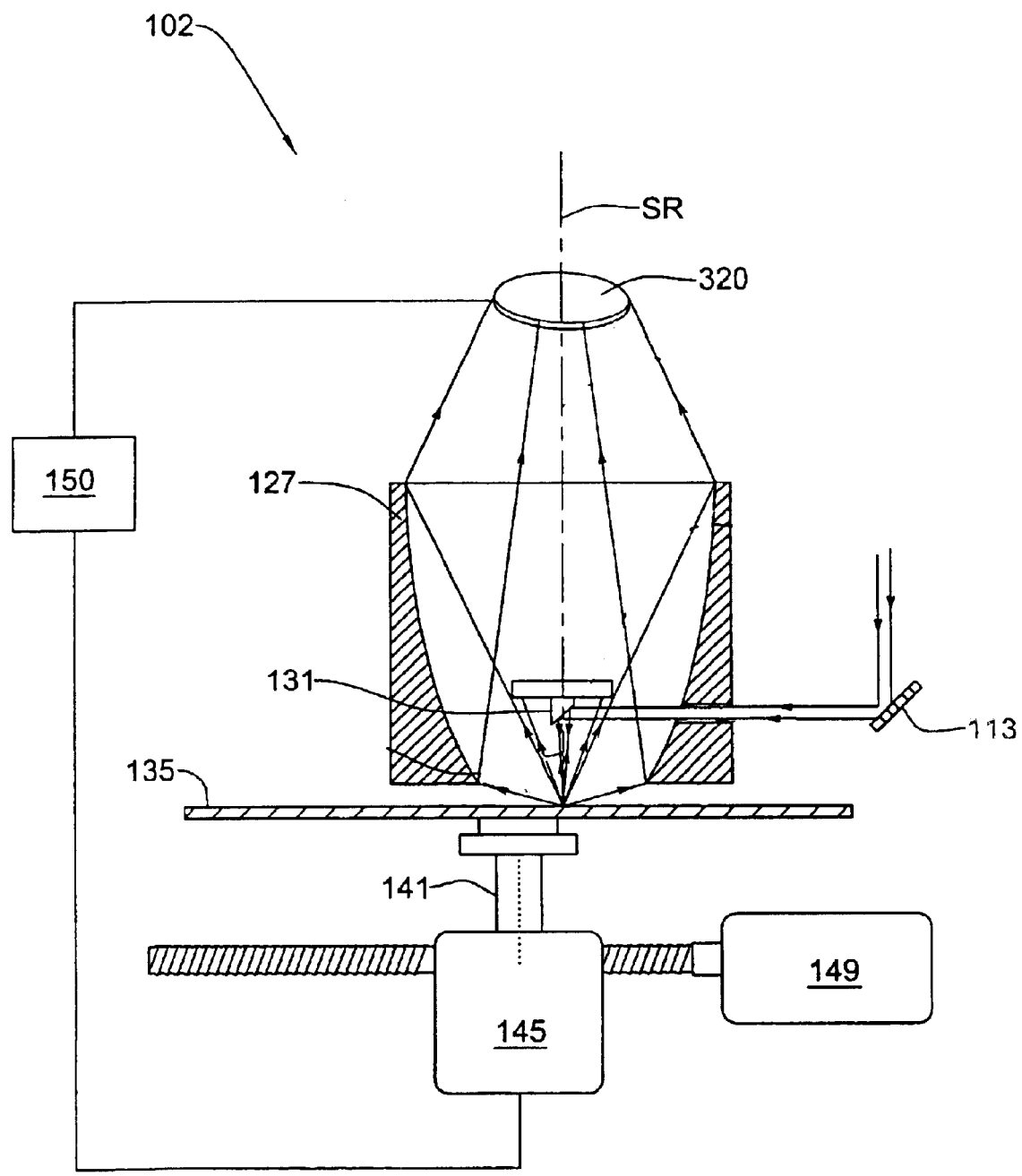
FIG. 2B shows a perspective view of an apparatus according to another embodiment of the present invention.

FIG. 2B shows apparatus 102 in accordance with another embodiment of the invention. Apparatus 102 is similar to apparatus 101, but has multiple detectors, such as detector array 320, instead of filter 310.

Figure 2C:
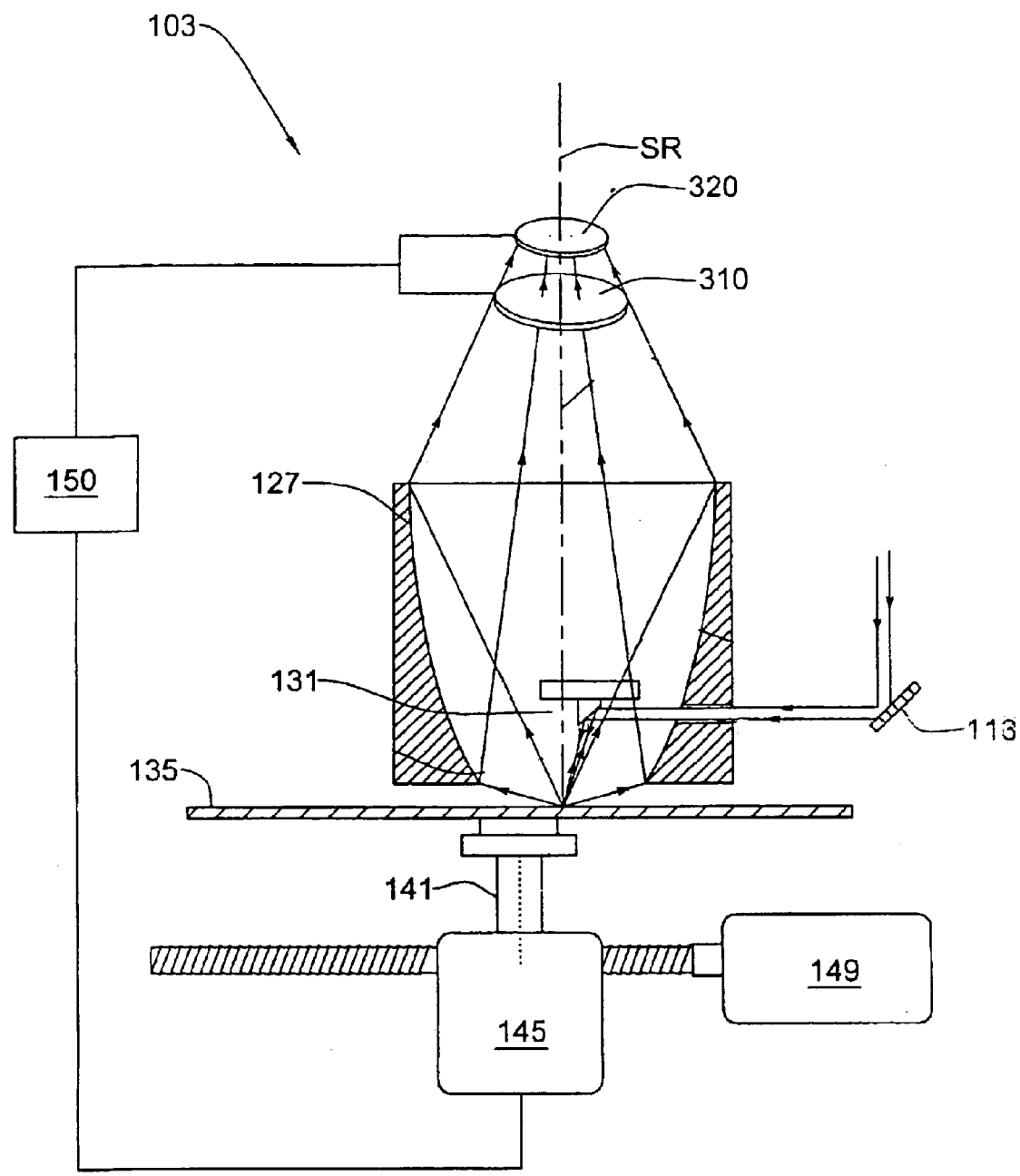
FIG. 2C shows a perspective view of an apparatus according to still another embodiment of the present invention.

FIG. 2C shows apparatus 103 in accordance with a further embodiment of the invention. Apparatus 103 is similar to apparatus 101 but has additional multiple detectors, such as detector array 320 located upstream in the paths of scattered and reflected light beams in relation to filter 310. The addition of these detectors enables to geometrically select the pattern of scattered light-rays to be detected, which improves the system's performance.

Note that although the light beam that impinges the wafer surface in the examples of FIGS. 2A and 2B is perpendicular to the surface, the invention is by no means bound by these specific embodiments, as exemplified in FIG. 2C. An exemplary embodiment where the light impinges the surface in a non-perpendicular fashion is described with reference to FIGS. 8C–D, below.

Further note that whereas for the convenience of explanation the description below concerns mainly a filter, it likewise applies to an array of filters.

It also should be noted that the invention is by no means bound by this specific embodiment. Thus, for example, in accordance with a modified embodiment, any of the previous embodiments can be modified, e.g. to include a first optical means that collimate the scattered light to be filtered and second optical means to focus the filtered beam before impinging on the detector. The first optical means can be used also for matching the diameter of the collimated beam to the diameter of the filter 310 or to the diameter of the detector array 320. Both optical means can be used also for fine-tuning the solid angle of the beam of light impinging on the filter and/or the detector. In still another modified embodiment a lens assembly is disposed between the input aperture and the exit aperture of ellipsoidal mirrored surface 127 to collect light reflected from the wafer surface and passing through the mirrored surface. The reflected light is then guided away from the filter to be blocked or used for further detection.

Generally speaking, when the wafer rotates, different dies on the wafer are exposed to the illumination spot for inspection purposes. Since all dies in the wafer have the same orientation, it readily arises that as the wafer rotates, the inspected die's pattern is oriented at a different angle for each rotation. Accordingly, by the embodiments of FIGS. 2A–2C, whichever the case may be, the filter 310 and/or detectors 320 should be rotated or reconfigured in synchronization with that of the wafer rotation such that the filter will substantially block the scattered light due to the pattern and, by the same token, the detectors will be substantially blocked from detection of the scattered light due to the pattern. In contrast, the filter should substantially pass scattered light due to defect(s) and by the same token, the detectors should substantially detect light due to defect(s). By "substantially" it is meant that not all scattered light due to defect(s) is passed or detected, which the case may be. To this end, a controller 150 is utilized, as will be explained in greater detail below.

Figure 3A:
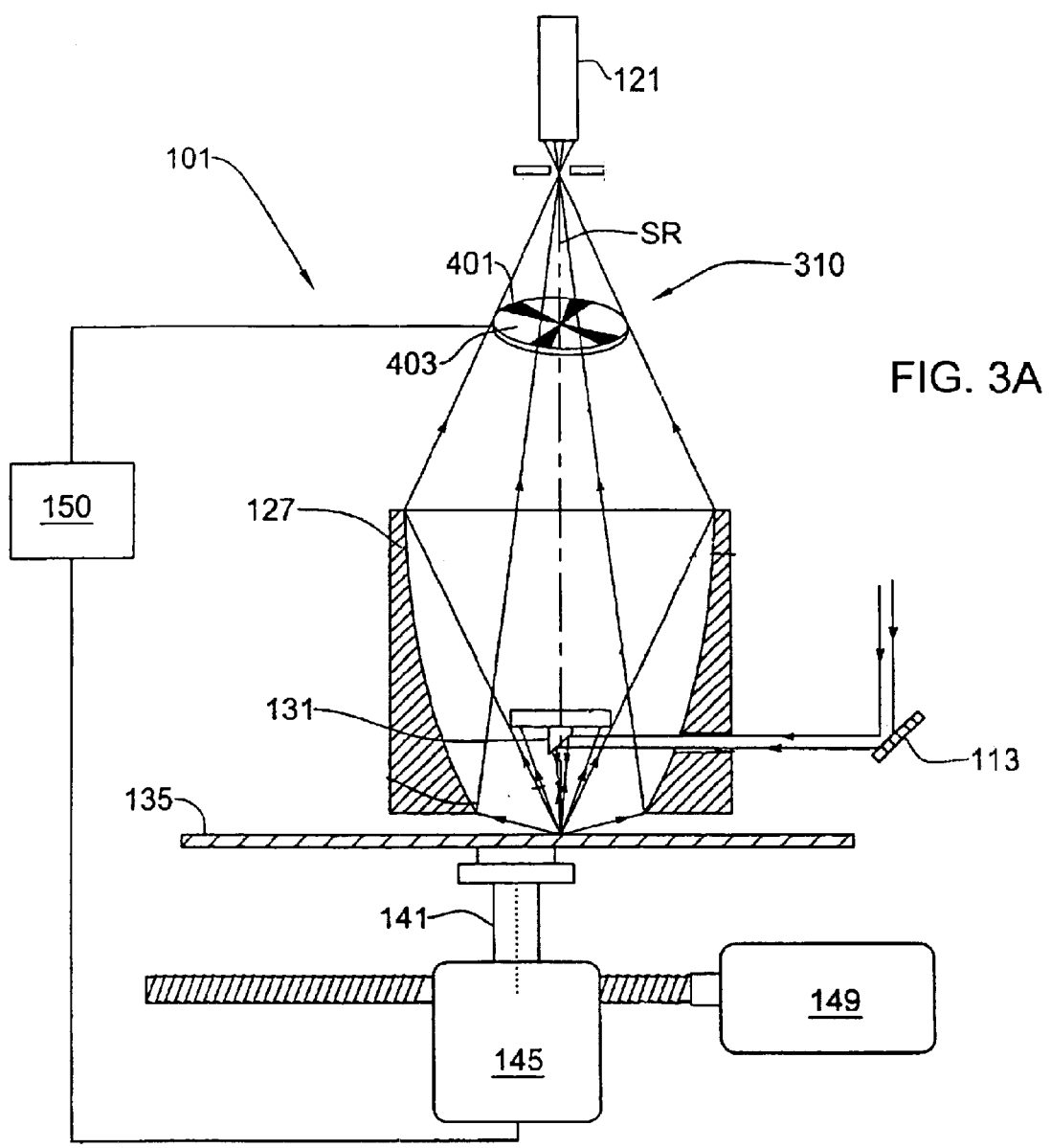
FIG. 3A shows a perspective view of a filter placed in the apparatus according to an embodiment of the present invention.

There are several ways to realize the above described process, as will now be explained with reference to FIG. 3. and onwards. As shown in FIG. 3A, apparatus 101 has filter 310 that includes disk 401, which is opaque to light. In the disk 401 there are apertures 403 at pre-defined locations such that scattered light due to defects can pass through said filter only through said apertures. A controller 150 that is coupled to both the disk 401 and rotation motor 145 is configured to rotate the disk about the axis of symmetry SR in a synchronized fashion with said motor, so as to let the light scattered from the defects pass through said apertures and be detected by the detector 121. The scattered light (or major portion thereof) due to the pattern, impinges on the opaque sectors 401 and is blocked thereby, and consequently, will not reach detector 121 and obviously will not be detected. Thus, the filter functions as a rigid mask to substantially block all scattered light rays due to the pattern in accordance with the (same) rotational movement of all the detectors.

It should be noted that, as known per se, the shape of the filter (e.g. in the form of disk), and in particular the pattern of apertures such as 403, is tailored to fit the pattern of the surface. Such filters are known in the art. Such a disk may be either designed e.g. in accordance with actual measurements of the distribution of light reflection due to pattern, or as a consequence of a mathematical model describing the reflection and scattering pattern from a specific wafer.

Further note that a filter bank can be prepared in advance for a variety of requirements. A filter assembly composed of several filters (e.g. in the form of a large disk that contains several filters along its perimeter) can be used as filter 403. For each type of patterned wafer, the most suitable filter on the filter assembly is chosen in accordance with actual measurements of the distribution of light reflection due to pattern received at the detector after being reflected by a each filter available on the assembly and selecting the most appropriate one.

The filter ensures that the scattered light rays that reach the detectors are mainly or wholly due to defects. The rotation of the filter is exemplified in FIGS. 3B–C.

Figure 3B:
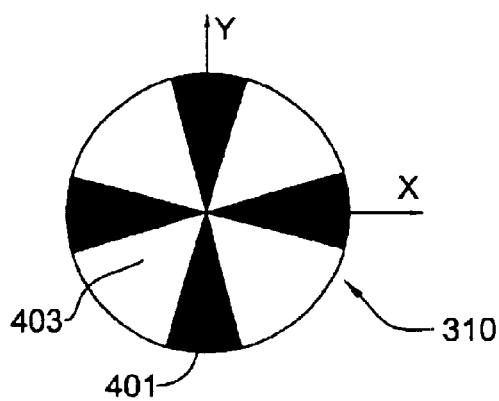
FIGS. 3B–C describe the rotation of the filter synchronized with the wafer's rotation, in accordance with an embodiment of the invention.
Figure 3C:
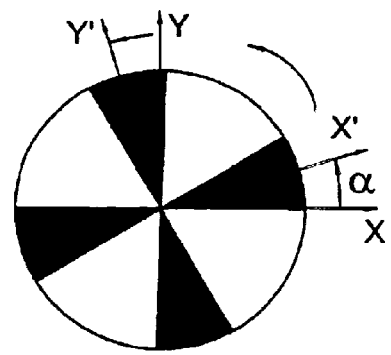

Those versed in the art will readily appreciate that the invention is not bound by the use of a disk with discrete apertures and particularly not to the disk described in FIGS. 3A–C.

Figure 4A:
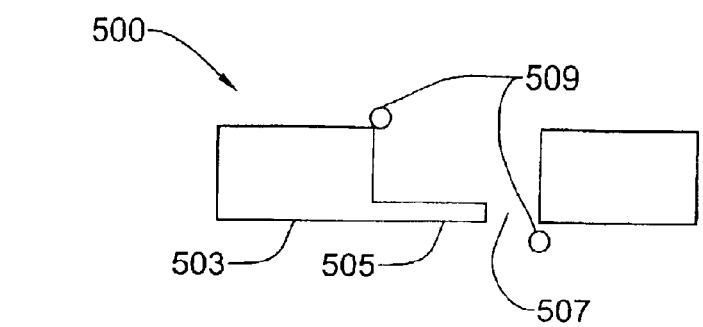
FIGS. 4A–B show a side view of a closed and open MEMS (Micro-Electro-Mechanical System), in accordance with an embodiment of the invention.
Figure 4B:
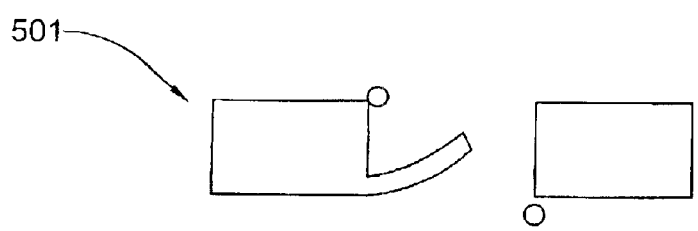
Figure 4C:
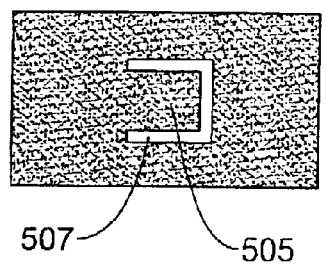
FIG. 4C shows a plan view if the MEMS illustrated in FIGS. 4A and 4B
Figure 4D:
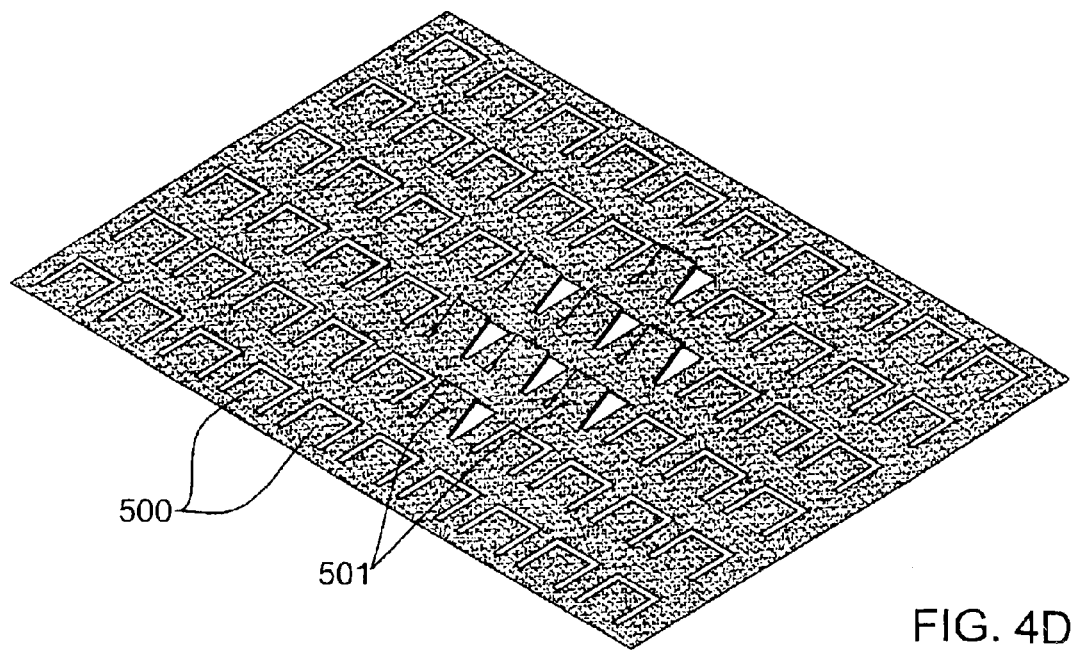
FIG. 4D shows a filter comprised of a 2D matrix of MEMS, in accordance with an embodiment of the invention.

Another non-limiting realization of a filter is the Micro-Electro-Mechanical System (MEMS) 2D array technique shown in FIGS. 4A–D. The MEMS array-of-shutters functions exactly as a filter described above with reference to FIGS. 3A–C, except for the fact that the rotation is done electronically Thus, FIG. 4A schematically describes the structure of a rectangular MEMS shutter. It is noted that other shaped MEMS arrays, such as circular MEMS arrays may be utilized. MEMS arrays are known in the art. FIGS. 4A–D illustrate a typical MEMS array. The etching of a thick silicon wafer bedding 500 produces a thin sheet of silicon 505 that is partially surrounded by a narrow spacing 507 and is also connected to a thick sheet of silicon 503. The narrow spacing 507 is generated by etching the whole silicon thick layer. Therefore, the thin sheet 505 is able to bend to some degree. The addition of electrodes 509 enables to realize the bending of the thin silicon sheet (FIG. 4B) or aligning it back (FIG. 4A), thus giving rise to an opening or closing of the shutter. The MEMS technique enables to produce a 2D array of, say, hundreds of shutters, a number large enough to make an effective filter for the purpose of the present invention, as shown schematically in FIG. 4D.

In order to block scattered light due to a die pattern, some of the shutters should be closed in a pattern that fits the pattern of said scattered light, i.e. scattered light due to the pattern should be blocked (by impinging on closed shutters) and scattered light due to defects should pass through open shutters, similar to the configuration described above, with reference to FIG. 3A. To this end, a controller of the kind described above should be employed to synchronize between the wafer rotation and the opening/closing of the MEMS shutters.

Those versed in the art will readily appreciate that the invention is not bound by the use of an array of shutters and particularly not to the MEMS array described in FIGS. 4A–D.

Another non-limiting realization of a filter is the Liquid Crystal Display (LCD) technique, presented in FIGS. 5A–C. As is generally known per se, LCD unit (or cell) is a device having a first polarizer and a second polarizer, both defining a space in which a liquid crystal is placed. A liquid crystal is fluid like a regular liquid but is anisotropic in its optical and electromagnetic characteristics like a solid, due to the high orientational order of the liquid crystal molecules (620 in FIG. 5A).

When plane-polarized light passes through a liquid crystal, the molecules of the liquid crystal rotate the plane of polarization of the light. Light that passes through the first polarizer 640 is polarized. The polarized light passes then through the liquid crystal, which rotates the plane of polarization of the passing light. The second polarizer 660 is placed at the exit of the liquid crystal. The orientation of the second polarizer is chosen to be parallel to the polarization of the light emanating from the liquid crystal (e.g. perpendicular to first polarizer, but in no case parallel to it). Thus, the liquid crystal guides the polarized light from the first polarizer so that the light may be transmitted through the second polarizer.

When an external voltage 610 is applied across a liquid crystal cell, the liquid crystal molecules (630 in FIG. 5B) are aligned in parallel to the electric field that is induced by the external voltage, and cannot rotate the plane of polarization of the passing light anymore. Thus, light cannot get out of the device any more. Therefore, applying a voltage on the LCD based device 601 in FIG. 5B blocks the light in analogy to the functioning of the MEMS device. The LCD 2D array in FIG. 5C functions similarly to the 2D MEMS array explained above, where voltage is activated (open) MEMS is functionally analog to a non-activated (open) LCD cell 600 and close MEMS is functionally analog to a voltage activated (close) LCD cell 601. The device uses a controller of the kind specified above to synchronize between the opening/closing of LCD shutters and the wafer rotation.

Those versed in the art will readily appreciate that the invention is not bound by the use of an array of shutters and particularly not to the liquid crystal array described in FIGS. 5A–C.

Note that the blocking of scattered light due to the die's pattern can be realized also by using an array of detectors. The array of detectors is adapted to detect scattered light substantially other than said scattered light due to a pattern. By one embodiment, this is realized in a way that the detectors in the array are switched on or off via a controller in a synchronized manner to the rotation of the wafer as in the case of a filter described with reference to FIG. 2A above. By way of another example, this may be realized by switching on all the detectors but reading under the control of the controller only data indicative of scattered light substantially other than said scattered light due to pattern Note that each detector has its own light collection zone. The light collection zones of different detectors may vary in shape, in size and/or in their direction. The light collection zones of neighboring detectors preferably partially overlap, so as to ensure coverage of the whole detection area.

There may be many realizations that utilize an array of detectors. There follows a description of two non-limiting embodiments.

In accordance with a first realization described with reference to FIG. 6A, detector array 320 includes a plurality of detectors collectively denoted 700 that are arranged in a ring shape. Such a device may include e.g. several tens of detectors, such as detectors 701 (e.g. Photo-multiplier Tubes (PMTs), Photodiodes, Avalanche Photodiodes), which is enough for obtaining considerable (but still rough) sensitivity to the rotation of dies.

Figure 6A:
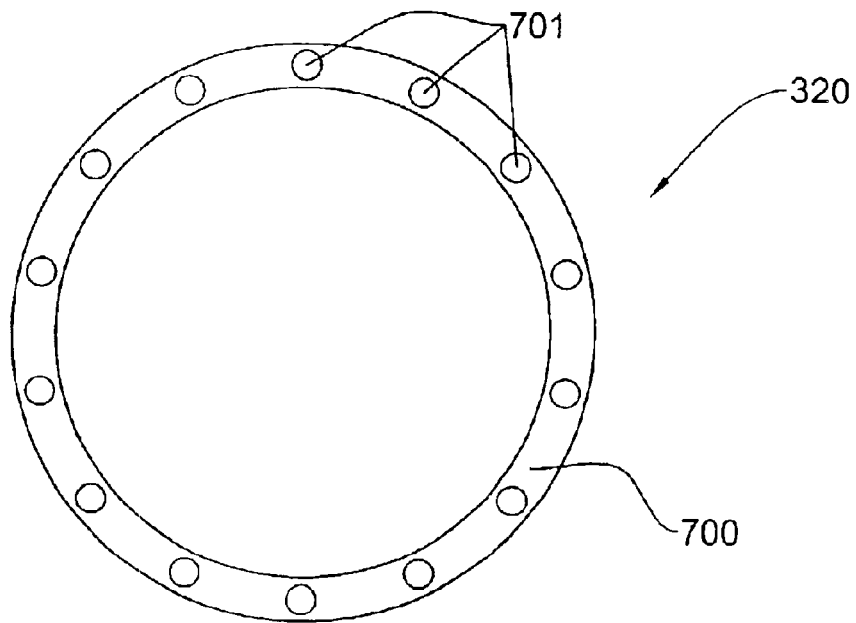
FIG. 6A shows a ring-shaped array of detectors, in accordance with an embodiment of the invention.
Figure 6B:
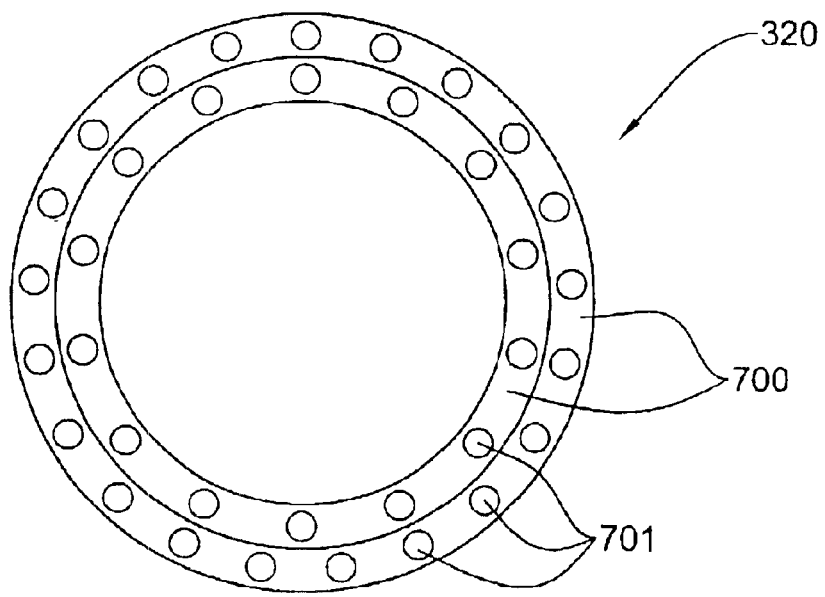
FIG. 6B shows concentric ring-shaped arrays of detectors, in accordance with an embodiment of the invention.

Detector array 320 may also include multiple detectors arranged as a few concentric rings, as illustrated at FIG. 6B. All the ringed arrays of detectors are concentrically placed at one plane and oriented towards the same location. This configuration enables to add more detectors and improves the configuration's sensitivity to the angular orientation of the die.

Those versed in the art will readily appreciate that the invention is not bound by the use of ringed arrays of detectors and particularly not to the array of detectors described in FIGS. 6A or 6B.

Figure 7A:
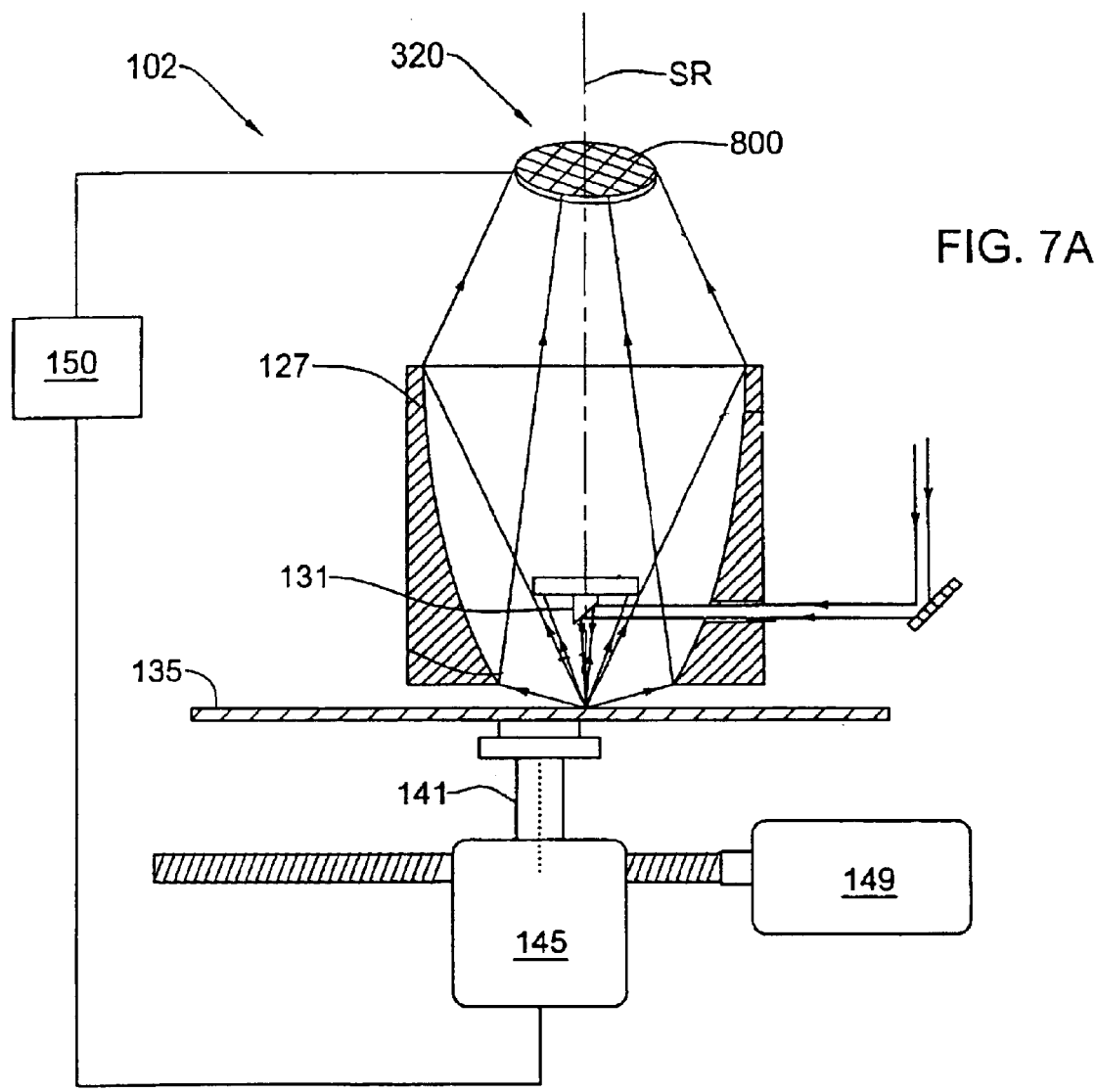
FIG. 7A shows a perspective view of an array of detectors made of CCDs, in accordance with an embodiment of the invention.
Figure 7B:
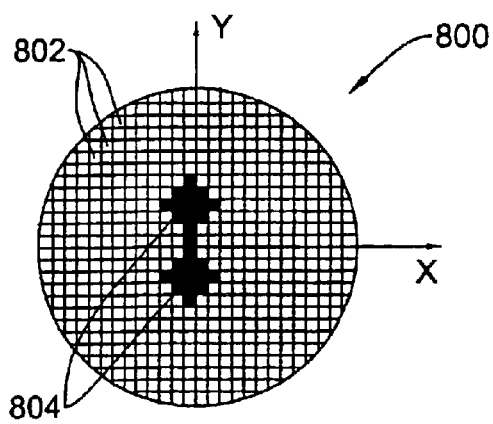
FIGS. 7B–C show respective opening and closing of CCDS according to wafer rotation, in accordance with the embodiment of FIG. 7A
Figure 7C:
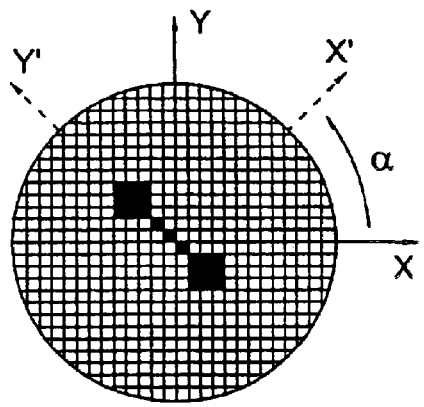

Another realization is shown in FIGS. 7A–C. FIG. 7A illustrates apparatus 102 in which detector array 320 includes a CCD array. A CCD array 800 is an array of light-sensitive elements 802, which are, in fact, some small electronic capacitors that are charged by the electrons that are generated by incident light. The array may be implemented by at least one CCD chip, each CCD chip including multiple CCD detecting elements. Common CCD chips are composed of a large number of detecting elements, referred to also as pixels (e.g. 192*165, 512*512, 1024*1024 or more). Thus, the use of a CCD array is advantageous as compared to an array of regular detectors, in that the number of detectors (i.e. cells) is enormously higher than in the former realization. This makes the CCD array much more accurate and sensitive to small angle rotations.

The main disadvantage of using a CCD array is the huge data rate delivered as an output of the CCD. The sampling rate of dies on a wafer is very high, typically, although not necessarily, about $10^7$ samples/sec. Thus, the data rate that should be delivered from a CCD is about $N*10^7$ pixels/sec, where N is the number of CCD elements. Since a typical CCD has about $10^4$–$10^6$ pixels, the expected output data rate is in the range of $10^{11}$–$10^{13}$ pixels/sec, which is well beyond the present technology. An example for a fast CCD array is the PB-MV40 Megapixel CMOS Image Sensor of Photobit Company, which is capable of a digital output of almost $10^9$ pixels/sec per second, at most one percent of the expected rate.

A non-limiting solution to the problem of the data-processing bottleneck is by reading only a partial set of elements at each sampling (e.g. 802, not 804), since, anyway, not all of them are required for collecting scattered light from defects. Note that a CCD array composed of a large number of CCD chips, each chip having its own light collection zone, can be partitioned so as to allow such a selection, by avoiding data collection from chips that get scattered light due to pattern. Still, the amount of information is huge, rendering the data processing relatively complicated.

Those versed in the art will readily appreciate that the invention is not bound by the use of a CCD array and particularly not to the CCD array described in FIGS. 7A–C.

Reverting now to FIG. 2C, it is possible to use both a filter and an array of detectors. This combination adds a degree of freedom to geometrically select the pattern of scattered light-rays to be detected. This choice can improve the system's performance.

Figure 8A:
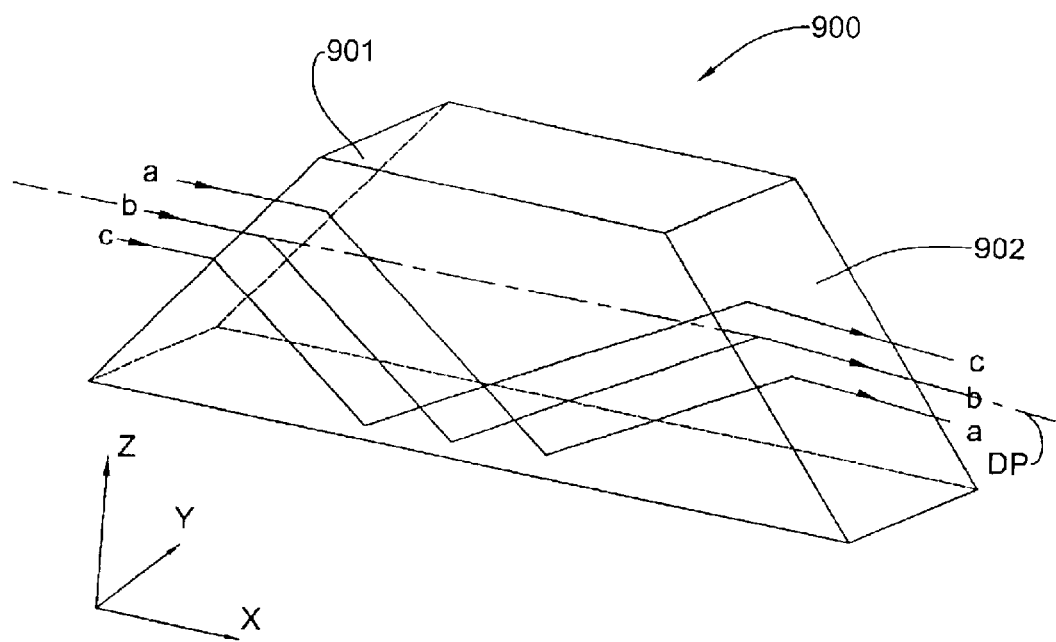
FIG. 8A illustrates the principle of operation of a Dove prism.
Figure 8B:
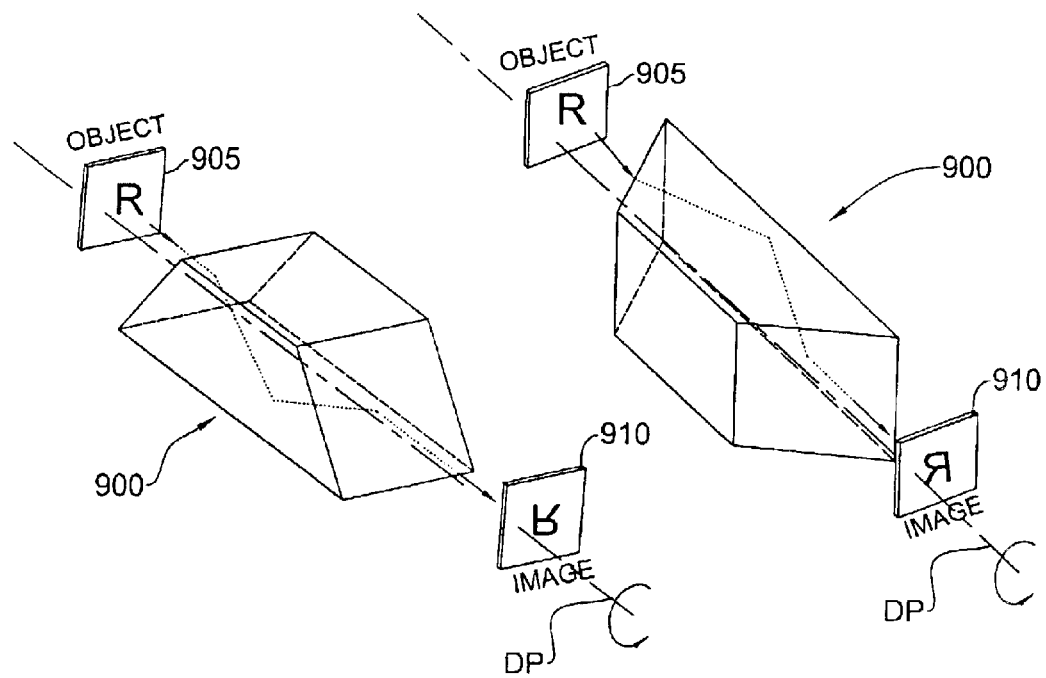
FIG. 8B further exemplifies the rotation of an image due to rotation of a Dove prism.

Another way to realize the apparatus according to the present invention, is by rotating the beam of scattered light at the outlet of the mirror 127, instead of rotating a filter or detector-array for the same purpose. This can be realized by using a Dove prism, whose principle of operation is schematically shown in FIG. 8A. A Dove prism is a prism whose triangular head is truncated. When light rays enter an incidental wall 901 of Dove prism 900, they get out of the other wall 902 in a reversed order. When the Dove prism 900 is rotated around an axis DP parallel to its base, as is shown in FIG. 8B, the entering image is rotated too at twice the angular velocity of the prism. This is illustrated in FIG. 8B, where the image 910 is rotated by 180° with reference to the object 905, as compared to a 90° rotation of Dove prism 900. Note that while rotating Dove prism 900 the field of view (e.g. an image 910 of a die on the wafer) is rotated too, but the-latter does not change its location within the wafer's surface. Thus, using Dove prism 900 obviates the need to rotate the filter in a controlled fashion or to control the detector array as discussed above.

The use of a dove prism 900 allows performing die to die defect analysis, as the dove prism rotation compensates for the wafers rotation. In other words, the dove prism provides substantially the same illumination and collection conditions, regardless the rotation of the wafer. An image of a die can be stored to be later compared to an image of another die or to a golden die.

Figure 8C:
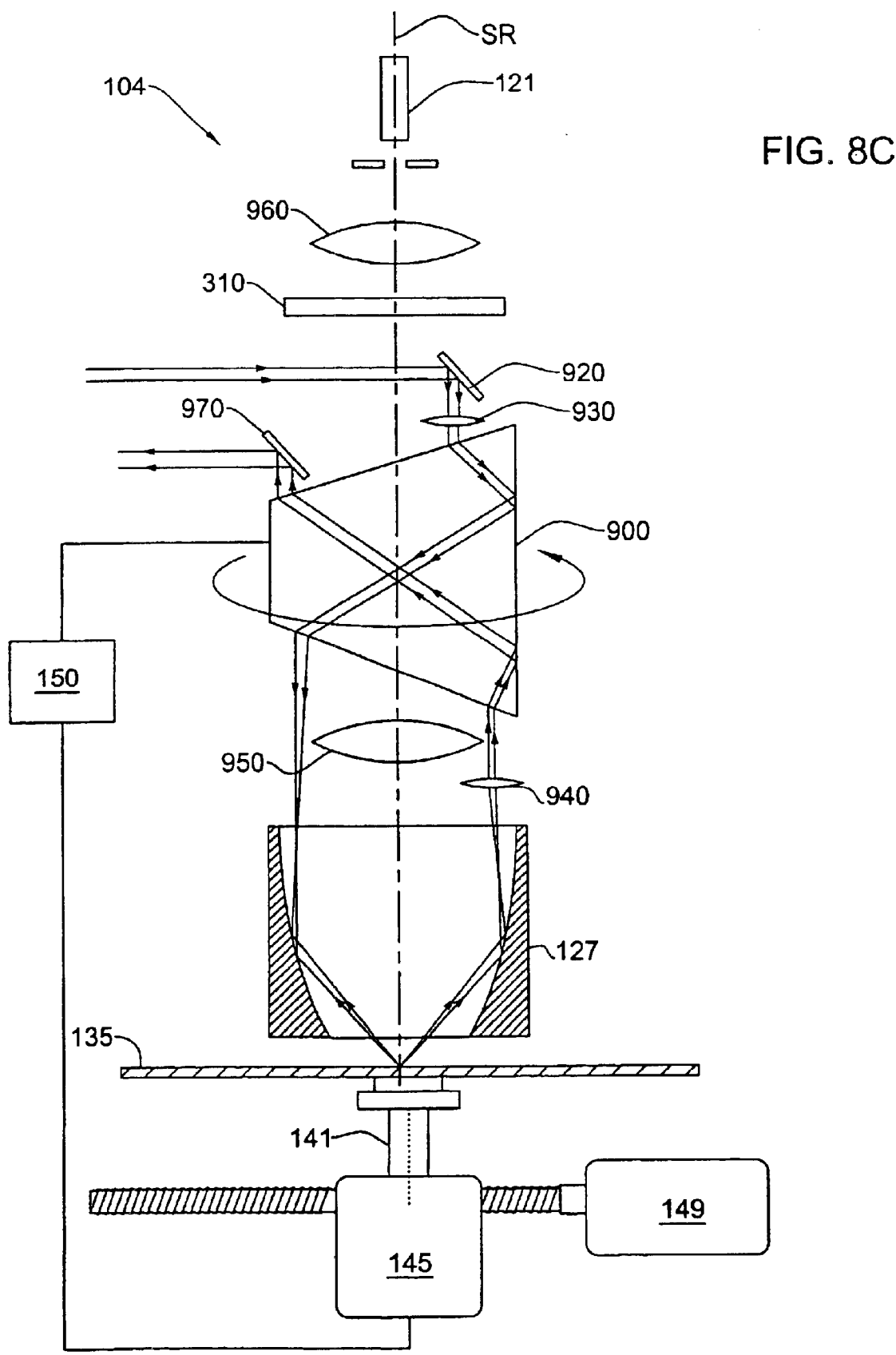
FIG. 8C shows a perspective view of an apparatus according to still another embodiment of the present invention, using a Dove prism between mirror to detector.
Figure 8D:
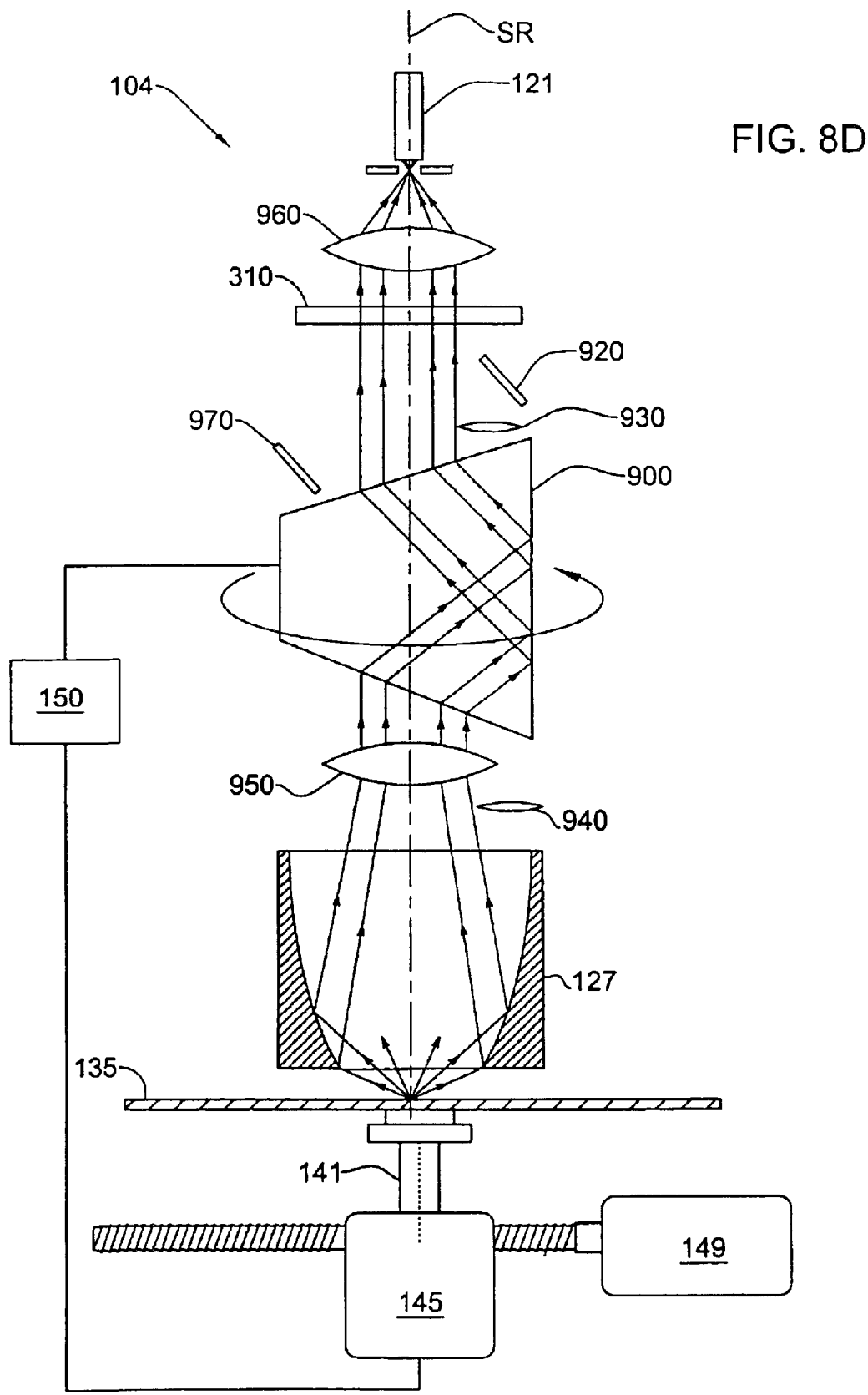
FIG. 8D illustrates the dark-field light beam in the system, showing the path through the optical system of the scattered rays due to pattern and defects.

FIGS. 8C and 8D illustrate apparatus 104, in accordance with a preferred embodiment of the invention. Apparatus 104 differs from apparatus 101 of FIG. 2A by setting Dove prism 900 disposed between the exit aperture of ellipsoidal mirror 127 and filter 310. In addition, lens assembly 930 is set for focusing the light beam onto the wafer surface and lens assembly 940 for collimating the light rays scattered from the wafer surface due to pattern and defects, while lens assembly 960 is set to focus the light at the outlet of filter 310 on detector 121. Note that lens assembly 950 is needed only when filter 310 is used for apparatus 104, but not in the alternative where detector array 320 is used. Note that controller 150 is required for rotating Dove prism 900 in a controlled fashion with the wafer rotation to compensate for the rotation of wafer pattern, as explained above.

Thus, according to one embodiment of the present invention, schematically illustrated in FIGS. 8C and 8D, Dove prism 900 is rotated at half the angular velocity of the wafer rotation in the opposite direction. The image at the exit of the Dove prism is a static image of a die, since the prism rotation compensates for the wafer rotation. The filter e.g. 310 or detectors array e.g. 320 as described above are placed at the exit of the Dove prism.

FIG. 8C describes the path of the bright-field light beam in the system. A beam of light is guided by mirror 920 to lens 930 that focuses the beam. The beam is guided through Dove prism 900 and the ellipsoidal mirror 127 onto the wafer surface. Lens 930 may be located also between Dove prism 900 and ellipsoidal mirror 127, on the condition that it has a ring shape, to allow the path of scattered rays upstream. The reflected beam is guided back through ellipsoidal mirror 127 to lens 940 that collimates the beam. The collimated beam passes through Dove prism 900 and is guided away by mirror 970 to be blocked or for further detection for other applications.

FIG. 8D describes the dark-field light beam in the system, showing the path through the optical system of the scattered rays due to pattern and defects. Lens assembly 950 and 960 form a relay assembly, which is intended to image the plane proximate to the wafer surface at a remote plane where the detector or detector array are located. Note that the detector (detectors array) are disposed relatively away from the surface (requiring thus the image at the remote plane) due to the relatively large size of the Dove prism. Relay assembly 950 and 960 enable to detect the image as if it were closer to the wafer. Lens assembly further matches the diameter of the collimated beam to the diameter of filter 310. The scattered light rays are collimated by lens assembly 950 to be guided through Dove prism 900. At the outlet of the Dove prism the collimated beam passes through filter 310 and then is focused by lens assembly 960 to impinge onto detector 121.

Note that other embodiments of Dove Prism are applicable. For example, instead of using filter 310 and detector 121, detectors array 320 is used. In still another embodiment of the present invention, filter 310 and detectors array 320 are used. The latter modifications are substantially similar to those described with reference to 101–103 in FIGS. 2A–C.

Further note that the embodiment of apparatus 104 has two advantages over the embodiments of apparatuses 101–103 illustrated with reference to FIGS. 2A–C. First, the image at the outlet of the Dove prism is static independent of the die's orientation. This means that the filter or the detector array gets practically the same distribution of light rays for each die. On the contrary, for the embodiments 101–103 the filter should be rotated in a controlled fashion (or the detector array operated in a controlled fashion) so as to match the image rotation. Thus, in the embodiments 101–103 unavoidable errors occur due to the limited resolution of the filter or of the detector array. The second advantage is that apparatus 104 is better adapted to use asymmetric light source, i.e. light source directed at a first angle in relation to the normal to the wafer surface (where the normal constitutes symmetry axis SR). For all the embodiments of FIGS. 2A–C, the use of an asymmetric light source necessarily entails the rotation of the light source in a synchronized fashion with the wafer rotation, thus maintaining the same orientation with the pattern of each die. Otherwise the filter or detector array would receive a totally different distribution of scattered light due to the pattern for each die. In contrast, in apparatus 104, as was explained above, the resulting image at the filter or detector array is static, due to the Dove prism, and therefore there is no need to rotate the light source.

Those versed in the art will readily appreciate that the invention is not bound by the use of a rotating prism and particularly not to the Dove prism described in FIGS. 8A–C.

The invention has been described with a certain degree of particularity. Those versed in the art will readily appreciate that the invention is not bound by the particular configurations described with reference to FIGS. 2 to 8 above or by the specific apparatus disclosed in the Marxer patent.

What is claimed is:

1. An optical system for detecting defects on a wafer that includes at least one pattern; the system comprising:

a source of light to produce a beam;

optics directing the beam along a path onto the wafer, producing an illuminated spot thereon;

at least one detector for detecting light;

an ellipsoidal mirrored surface, said mirrored surface and the at least one detector having an axis of symmetry about a line perpendicular to the wafer surface, said mirrored surface defining an input aperture positioned proximate to the wafer surface to receive scattered light therethrough from the wafer surface; said mirrored surface further defining an exit aperture and being substantially rotationally symmetric about said axis of symmetry, so that the mirrored surface reflects and focuses rotationally symmetrically about said axis of symmetry light that passes through the input aperture to the at least one detector; said exit aperture being located opposite to the input aperture; and at least one filter located between said exit aperture and said at least one detector, and being configured to substantially block a portion of the scattered light corresponding to the at least one pattern of the wafer and to substantially pass to said at least one detector another portion of the scattered light substantially other than the scattered light corresponding to the at least one pattern of the wafer.

2. The optical system of claim 1, wherein the at least one filter comprises a disk with apertures at pre-defined locations and being rotated, under a control of a controller, about said axis of symmetry; said controller is configured to rotate said filter so as to pass to the at least one detector, through said apertures, scattered light rays substantially other than said scattered light part to be detected by the at least one detector.

\* \* \* \* \*